US011890021B2

(12) United States Patent
Mac An Tuile et al.

(10) Patent No.: US 11,890,021 B2
(45) Date of Patent: *Feb. 6, 2024

(54) SURGICAL SAGITTAL BLADE CARTRIDGE WITH A REINFORCED GUIDE BAR

(71) Applicant: Stryker European Operations Holdings LLC, Kalamazoo, MI (US)

(72) Inventors: Conor Mac An Tuile, Muine Bheag (IE); James G. Walen, Portage, MI (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/572,022

(22) Filed: Jan. 10, 2022

(65) Prior Publication Data

US 2022/0125439 A1 Apr. 28, 2022

Related U.S. Application Data

(63) Continuation of application No. 16/907,197, filed on Jun. 20, 2020, now Pat. No. 11,241,240, which is a
(Continued)

(51) Int. Cl.
*A61B 17/14* (2006.01)
*B23D 51/16* (2006.01)
(Continued)

(52) U.S. Cl.
CPC ............ *A61B 17/142* (2016.11); *A61B 17/14* (2013.01); *B23D 51/16* (2013.01); *B23D 61/006* (2013.01); *B27B 19/006* (2013.01)

(58) Field of Classification Search
CPC ...... A61B 17/14; A61B 17/142; B23D 51/16; B23D 61/006; B23D 49/007;
(Continued)

(56) References Cited

U.S. PATENT DOCUMENTS

| 306,285 A | 10/1884 | Rigby et al. |
| 683,924 A | 10/1901 | Fraser |

(Continued)

FOREIGN PATENT DOCUMENTS

| AU | 2005292140 B2 | 7/2012 |
| CH | 654196 A5 | 2/1986 |

(Continued)

OTHER PUBLICATIONS

English language abstract and machine-assisted English translation for CN 101791235 extracted from espacenet.com database on Jul. 20, 2020, 6 pages.
(Continued)

*Primary Examiner* — Tracy L Kamikawa
(74) *Attorney, Agent, or Firm* — Howard & Howard Attorneys PLLC

(57) ABSTRACT

A surgical sagittal saw cartridge that includes a guide bar formed from an inner plate and opposed outer plates, the inner plate defining a head. The cartridge has a blade that is disposed against the head of the inner plate. The inner plate may comprise an inner tine and/or two opposed outer tines. The inner tine may be formed to define the head against which the blade is disposed. The outer tines may extend distally so as to define a space between the outer tines in which the blade is seated.

10 Claims, 5 Drawing Sheets

Related U.S. Application Data continuation of application No. 15/807,961, filed on Nov. 9, 2017, now Pat. No. 10,687,823, which is a continuation of application No. PCT/US2016/031407, filed on May 9, 2016.

(60) Provisional application No. 62/160,234, filed on May 12, 2015.

(51) Int. Cl.
 *B27B 19/00* (2006.01)
 *B23D 61/00* (2006.01)

(58) Field of Classification Search
 CPC ...... B23D 49/008; B23D 49/10; B23D 49/16; B23D 49/162; B23D 49/165; B23D 49/167; B23D 51/01; B23D 51/02; B23D 51/025; B23D 51/08; B23D 51/10; B23D 51/163; B23D 51/166; B27B 19/006; Y10T 83/8873; Y10T 83/8874; Y10T 83/8876; Y10T 83/8877; B23B 19/00; B23B 19/002; B23B 19/004; B23B 19/006; B23B 19/008; B23B 19/09
 USPC .................................................. 30/392–394
 See application file for complete search history.

(56) References Cited

U.S. PATENT DOCUMENTS

| | | |
|---|---|---|
| 1,201,467 A | 10/1916 | Hogland |
| 1,543,195 A | 6/1925 | Thugesen et al. |
| 1,708,133 A | 4/1929 | Comparetto |
| 2,138,862 A | 12/1938 | Johnston |
| 2,702,550 A | 2/1955 | Rowe et al. |
| 2,854,981 A | 10/1958 | Morrison |
| 3,495,590 A | 2/1970 | Zeiller |
| 3,642,002 A | 2/1972 | Otterstrom |
| 3,678,934 A | 7/1972 | Warfield et al. |
| 3,734,652 A | 5/1973 | Barnett |
| 3,797,497 A | 3/1974 | Crim et al. |
| 3,835,859 A | 9/1974 | Roberts et al. |
| 3,882,737 A | 5/1975 | Crim et al. |
| 3,905,105 A | 9/1975 | Tuke |
| 3,978,862 A | 9/1976 | Morrison |
| 4,019,408 A | 4/1977 | Idel |
| 4,184,804 A | 1/1980 | Inagaki et al. |
| 4,203,444 A | 5/1980 | Bonnell et al. |
| 4,217,964 A | 8/1980 | Eaton |
| 4,246,902 A | 1/1981 | Martinez |
| 4,273,169 A | 6/1981 | Baenen |
| 4,274,414 A | 6/1981 | Johnson et al. |
| 4,461,296 A | 7/1984 | Hodge |
| 4,502,184 A | 3/1985 | Karubian |
| 4,513,742 A | 4/1985 | Amegger |
| 4,584,999 A | 4/1986 | Amegger |
| 4,637,391 A | 1/1987 | Schlein |
| 4,683,924 A | 8/1987 | Cornelius |
| 4,700,702 A | 10/1987 | Nilsson |
| 4,708,133 A | 11/1987 | Comparetto |
| 4,892,093 A | 1/1990 | Zarnowski et al. |
| 4,941,466 A | 7/1990 | Romano |
| 5,014,430 A | 5/1991 | Wortham |
| 5,092,869 A | 3/1992 | Waldron |
| 5,100,506 A | 3/1992 | Sturtevant et al. |
| 5,122,142 A | 6/1992 | Pascaloff |
| 5,133,728 A | 7/1992 | Petersen |
| 5,135,533 A | 8/1992 | Petersen et al. |
| 5,178,626 A | 1/1993 | Pappas |
| 5,265,343 A | 11/1993 | Pascaloff |
| 5,306,285 A | 4/1994 | Miller et al. |
| 5,349,754 A | 9/1994 | Wuensch et al. |
| 5,423,822 A | 6/1995 | Hershberger et al. |
| 5,439,472 A | 8/1995 | Evans et al. |
| 5,468,247 A | 11/1995 | Matthai et al. |
| 5,496,325 A | 3/1996 | McLees |
| 5,591,170 A | 1/1997 | Spievack et al. |
| 5,609,603 A | 3/1997 | Linden |
| 5,697,158 A | 12/1997 | Klinzing et al. |
| 5,725,530 A | 3/1998 | Popken |
| 5,735,866 A | 4/1998 | Adams et al. |
| 5,817,097 A | 10/1998 | Howard et al. |
| 5,846,244 A | 12/1998 | Cripe |
| 5,897,570 A | 4/1999 | Palleva et al. |
| 6,001,115 A | 12/1999 | Ahola et al. |
| 6,105,535 A | 8/2000 | Atamian et al. |
| 6,106,535 A | 8/2000 | Dross et al. |
| 6,113,618 A | 9/2000 | Nic |
| 6,860,886 B1 | 3/2005 | Lee |
| 6,875,222 B2 | 4/2005 | Long et al. |
| 6,949,110 B2 | 9/2005 | Ark et al. |
| 6,960,894 B2 | 11/2005 | Carusillo et al. |
| 7,362,228 B2 | 4/2008 | Nycz et al. |
| 7,497,860 B2 * | 3/2009 | Carusillo ............ A61B 17/157 606/86 R |
| 7,638,958 B2 | 12/2009 | Philipp et al. |
| 7,691,106 B2 | 4/2010 | Schenberger et al. |
| 7,704,254 B2 | 4/2010 | Walen |
| 7,744,616 B2 | 6/2010 | O'Donoghue |
| 7,748,308 B2 | 7/2010 | Anderson et al. |
| 8,043,292 B2 | 10/2011 | Carusillo |
| 8,323,285 B2 | 12/2012 | Walen et al. |
| 8,403,932 B2 | 3/2013 | Carusillo et al. |
| 8,444,647 B2 | 5/2013 | Walen et al. |
| 8,672,943 B2 * | 3/2014 | Fisher ................. A61B 17/142 606/82 |
| 8,696,673 B2 | 4/2014 | Walen et al. |
| 8,702,710 B2 | 4/2014 | Carusillo |
| 9,060,783 B2 | 6/2015 | Walen et al. |
| 9,072,526 B2 | 7/2015 | Carusillo |
| 9,192,390 B2 | 11/2015 | delRio et al. |
| 9,554,808 B2 | 1/2017 | Carusillo |
| 9,820,753 B2 | 11/2017 | Walen et al. |
| 9,848,887 B2 | 12/2017 | Carusillo et al. |
| 10,251,651 B2 | 4/2019 | Carusillo |
| 10,278,710 B2 | 5/2019 | Walen et al. |
| 10,687,823 B2 * | 6/2020 | Mac an Tuile ........ A61B 17/14 |
| 11,160,561 B2 | 11/2021 | MacAn Tuile et al. |
| 11,241,240 B2 * | 2/2022 | Mac An Tuile ..... A61B 17/142 |
| 2002/0116022 A1 | 8/2002 | Lebouitz et al. |
| 2002/0198556 A1 | 12/2002 | Ark |
| 2003/0093103 A1 | 5/2003 | Malackowski et al. |
| 2005/0020909 A1 | 1/2005 | Moctezuma de la Barrera et al. |
| 2006/0009796 A1 | 1/2006 | Carusillo et al. |
| 2006/0111723 A1 | 5/2006 | Chapolini et al. |
| 2007/0068399 A1 | 3/2007 | Anderson et al. |
| 2007/0083209 A1 | 4/2007 | Schenberger et al. |
| 2007/0085496 A1 | 4/2007 | Philipp et al. |
| 2007/0119055 A1 | 5/2007 | Walen et al. |
| 2008/0119860 A1 | 5/2008 | McCarthy |
| 2010/0292701 A1 | 11/2010 | Fisher et al. |
| 2014/0163558 A1 | 6/2014 | Cosgrove et al. |
| 2014/0194882 A1 | 7/2014 | Walen et al. |
| 2019/0201003 A1 | 7/2019 | Carusillo |
| 2019/0231364 A1 | 8/2019 | Walen et al. |
| 2020/0315632 A1 | 10/2020 | Mac An Tuile et al. |

FOREIGN PATENT DOCUMENTS

| | | |
|---|---|---|
| CN | 1045026 A | 9/1990 |
| CN | 101791235 A | 8/2010 |
| CN | 102826549 A | 12/2012 |
| CN | 103505259 A | 1/2014 |
| CN | 103860232 A | 6/2014 |
| DE | 354343 C | 6/1922 |
| DE | 478354 C | 6/1929 |
| DE | 2400696 B2 | 8/1976 |
| DE | 2615301 A1 | 10/1977 |
| DE | 2628131 A1 | 12/1977 |
| DE | 2611720 B2 | 5/1978 |
| DE | 2640267 A1 | 5/1978 |
| DE | 2935732 A1 | 3/1981 |
| DE | 3640516 C1 | 4/1988 |
| DE | 3638404 A1 | 5/1988 |

(56) References Cited

FOREIGN PATENT DOCUMENTS

| | | |
|---|---|---|
| DE | 8906511 U1 | 7/1989 |
| DE | 4140395 A1 | 6/1993 |
| DE | 102008062880 A1 | 6/2010 |
| EP | 1880682 A2 | 1/2008 |
| FR | 2651114 B1 | 10/1991 |
| GB | 2317510 A | 3/1998 |
| RU | 2218112 C2 | 12/2003 |
| WO | 2004105623 A1 | 12/2004 |
| WO | 2006017066 A2 | 2/2006 |
| WO | 2006063156 A1 | 6/2006 |
| WO | 2007030793 A2 | 3/2007 |
| WO | 2007045993 A2 | 4/2007 |
| WO | 2008024717 A2 | 2/2008 |

OTHER PUBLICATIONS

English language abstract and machine-assisted English translation for CN 102826549 extracted from espacenet.com database on Jul. 20, 2020, 5 pages.

English language abstract and machine-assisted English translation for CN 1045026 extracted from espacenet.com database on Jul. 20, 2020, 5 pages.

English language abstract and machine-assisted English translation for DE 2008 062 880 extracted from espacenet.com database on Dec. 11, 2017, 28 pages.

English language abstract for CN 103860232 extracted from espacenet.com database on Jul. 20, 2020, 1 page.

International Search Report for Application No. PCT/US2016/031407 dated Jan. 10, 2017, 6 pages.

SA Search Report and Written Opinion for PCT/US2016/031407, dated Oct. 1, 2017.

English Language abstract and computer-generated English language translation for FR 2651114 B1 extracred from espacenet.com database on Dec. 3, 2020, 9 pages.

English Language abstract and machine-assisted English language translation for FR 2 651 114 B1 extracred from espacenet.com databse on Feb. 27, 2021, 9 pages.

English language abstract and machine-assisted English translation for DE 2611720 B2 extracted from espacenet.com database on Feb. 17, 2021, 6 pages.

English language abstract and machine-assisted English translation for DE 2628131 A1 extracted from espacenet.com database on Feb. 17, 2021, 5 pages.

English language abstract and machine-assisted English translation for DE 2640267 A1 extracted from espacenet.com database on Feb. 17, 2021, 4 pages.

English language abstract and machine-assisted English translation for DE 2935732 A1 extracted from espace523net.com database on Feb. 17, 2021, 10 pages.

English language abstract and machine-assisted English translation for DE 3638404 A1 extracted from espacenet.com database on Feb. 17, 2021, 9 pages.

English language abstract and machine-assisted English translation for DE 3640516 C1 extracted from espacenet.com database on Feb. 17, 2021, 6 pages.

English language abstract and machine-assisted English translation for EP 1 880 682 A2 extracted from espacenet.com database on Aug. 29, 2018, 33 pages.

English language abstract and machine-assisted English translation for RU 2218112 C2 extracted from espacenet.com database on Feb. 17, 2021, 5 pages.

English language abstract and machine-assisted English translation for WO 2004/105623 A1 extracted from espacenet.com database on Feb. 17, 2021, 14 pages.

English language abstract for DE 4140395 A1 extracted from espacenet.com database on Feb. 17, 2021, 2 pages.

English language abstract for WO 03/013771 A1 extracted from espacenet.com databa523se on Feb. 17, 2021, 1 page.

English language abstract not found for CH 654196 A5; however, see English language equivalent U.S. Pat. No. 4,513,742. Original document extracted from espacenet.com database on Feb. 17, 2021, 4 pages. cited 523by applicant.

English language abstract not found for DE 2400696 B2; however, see English language equivalent U.S. Pat. No. 3,905,105. Original document extracted from espacenet.com database on Feb. 17, 2021, 20 pages.

International Search Report for PCT App. No. PCT/US2006/035204, dated Jul. 2007.

International Search Report for PCT/US2005/023769, dated Feb. 22, 2006.

Machine-Assisted English translation for DE 2615301 A1 extracted from the espacenet.com database on Feb. 17, 2021, 6 pages.

Machine-Assisted English translation for DE 354343 C extracted from the espacenet.com database on Feb. 17, 2021, 3 pages.

Machine-Assisted English translation for DE 478354 C extracted from the espacenet.com database on Feb. 17, 2021, 4 pages.

Machine-Assisted English translation for DE 8906511 U1 extracted from the espacenet.com database on Feb. 17, 2021, 10 pages.

Stryker Corporation, Opposition Against EP Pat. No. 1 880 682 B1, dated Jan. 2011, 10 pages.

* cited by examiner

SURGICAL SAGITTAL BLADE CARTRIDGE WITH A REINFORCED GUIDE BAR

CROSS-REFERENCE TO RELATED APPLICATIONS

The present application is a continuation of U.S. patent application Ser. No. 16/907,197, filed on Jun. 20, 2020, now U.S. Pat. No. 11,241,240, which is a continuation of U.S. patent application Ser. No. 15/807,961, now U.S. Pat. No. 10,687,823, filed on Nov. 9, 2017, which is a continuation of PCT International Application No. PCT/US2016/031407, filed on May 9, 2016, which claims priority to and all the benefits of U.S. Provisional Patent Application No. 62/160,234, filed on May 12, 2015, all of which are hereby expressly incorporated herein by reference in their entirety.

FIELD OF THE INVENTION

This invention relates to a surgical sagittal blade cartridge that has a static guide bar and a blade head that is pivotally mounted to the guide bar. More particularly, this invention is related to a surgical sagittal blade cartridge with a reinforced guide bar.

BACKGROUND OF THE INVENTION

A sagittal saw blade is a surgical saw with a head that pivots around an axis that is perpendicular to the blade. PCT Pub. No. WO 2006/017066A2/U.S. Pat. No. 7,497,860 and PCT Pub. No. WO 2007/030793A2/U.S. Pat. No. 7,704,254, the contents of which are each incorporated herein by reference, each disclose a sagittal saw blade cartridge. A sagittal saw blade cartridge includes a static guide bar and a blade head. The guide bar is an elongated member that is releasably attached to the handpiece, the saw that actuates the cartridge. The blade head is pivotally mounted to the guide bar and has teeth that extend forward from the guide bar. One or more drive links extend from the blade head towards the proximal end of the guide bar. The drive links are reciprocated back and forth by a drive assembly internal to the saw. The reciprocation of the drive links causes the blade head to pivot back and forth. The pivoting of the blade head is what enables the teeth to cut the tissue against which the blade head is pressed. Sometimes, this type of cartridge is referred to as an oscillating tip saw blade cartridge.

An advantage of the sagittal blade cartridge is that the only portion of the cartridge that pivots is the distally located blade head. By way of comparison, a conventional sagittal saw blade pivots from its point of attachment to the saw to which the blade is attached. A cartridge, when actuated, vibrates less in the hands of the surgeon holding the handpiece. Also, it is common practice to use a cutting guide to properly position a sagittal saw blade relative to the tissue the blade is intended to cut. When a conventional blade is actuated, the oscillating movement of the blade imposes significant wear on the surfaces of the cutting guide defining the slot in which the blade is seated. The guide bar of a surgical sagittal blade cartridge only minimally moves in this slot. Thus, by using a cartridge, instead of a conventional blade, less of the material forming the cutting guide is rubbed off the guide. This reduces the extent to which the surgeon has to flush worn off cutting guide material from the surgical site. Further, use of the oscillating tip blade reduces the extent to which the material forming the guide becomes so worn that the guide itself is rendered useless.

A surgical sagittal blade cartridge has another benefit over a conventional sagittal saw blade. Since the guide bar remains static when the blade head is actuated, the practitioner can press a finger or two against the guide bar. This facilitates the holding of the cartridge in the desired position as the cartridge is advanced against the tissue that is to be cut.

When either a conventional sagittal blade or a sagittal blade cartridge advances through bone, the blade head is exposed to resistance. This resistance can be appreciable when the cut has a depth of 5 cm or more. Often the bone located adjacent the underside of the cartridge is more resistive to cutting than the bone located immediately above the cartridge. The cartridge, like most mechanical devices, will when advanced forward, advance along the path of least resistance. Since the bone above the cartridge can be less resistance to cutting than the bone below the cartridge, a cartridge when advanced, can flex upwardly out of the plane of the desired cut. This upwardly flexing of the blade is known as skiving. There can also be situations when owing to the density of the bone, the cartridge, when advanced, flexes below the plane of the cut. This type of flexure is known as diving.

Regardless of the direction the blade flexes, the flexure is undesirable. This is because a sagittal saw blade cartridge is typically used to remove bone so an artificial implant can be fitted in the space previously occupied by the removed bone. An implant is formed with surfaces designed to precisely seat against the complementary surfaces of the bone against which the implant is mounted. If the cut does not leave the bone with surfaces that have the desired shape, the results of the implant fitting procedure may be less than optimal.

In theory, one could increase the rigidity of a surgical sagittal blade cartridge by increasing the thickness of the guide bar. It should be appreciated that the slots of cutting guide through which the cartridge is inserted tend to be relatively narrow. Often the height this slots is around 1.5 mm or less. This height limit imposes a limit of the thickness of the cartridge guide bar that can be inserted in this slot. Furthermore, if thickness of the guide bar is increased, by extension it is necessary to increase the thickness of the cut that will be formed by the cartridge. Increasing cut thickness can also lead to the cartridge leaving a cut surface that does not have the desired degree of planar smoothness. Increasing guide bar thickness is therefore typically not a viable solution for reducing the incidence of cartridge flexure.

SUMMARY OF THE INVENTION

This invention is related to a new and useful surgical sagittal blade cartridge. The surgical sagittal blade cartridge includes a guide bar designed to resist deformation when subjected to uneven resistance.

The surgical sagittal blade cartridge of this invention includes a guide bar that is formed with three plates. There is a top plate and a bottom plate opposite the top plate. Between the top and bottom plate there is an inner plate. The inner plate is formed to have a curved head. The curved head functions as the boss around which the cartridge blade head pivots.

In many versions of the invention, the inner plate is formed to have a base that forms proximal end of the plate. Three tines extend forward from the base. There are two outer tines and an inner tine. The tines are laterally spaced apart from each other. The inner tine formed to have a curved head that functions as the pivot boss. When a cartridge with this type of guide bar is assembled, the drive links that pivot the blade head are disposed in the spaces between the inner tine and the outer tine.

In some versions of this invention, the outer tines extend distally forward of the inner tine. In these versions of the invention, the outer tines thus extend forward of the pivot boss. It should be appreciated that in these versions of the invention the base of the blade head is disposed between the spaced apart sections of the outer tine that are located forward of the pivot boss.

In versions of the invention where the outer tines extend forward of the inner tine, the outer tines may be formed with lobes that extend inwardly towards each other. These distal sections of the outer tine thus reinforces the guide bar so as to reduce the likelihood of the flexing of the guide bar.

In some versions of the invention the plates forming the guide bar are three distinct plates. These plates are welded or otherwise secured together to form the guide bar. In some versions of the invention two or more of the plates are machined, molded or otherwise formed as a single unit.

BRIEF DESCRIPTION OF THE DRAWINGS

The invention is pointed out with particularity in the claims. The above and further features and benefits of this invention are understood from the following Detailed Description taken in conjunction with the accompanying drawings in which:

DETAILED DESCRIPTION

Figure 1:
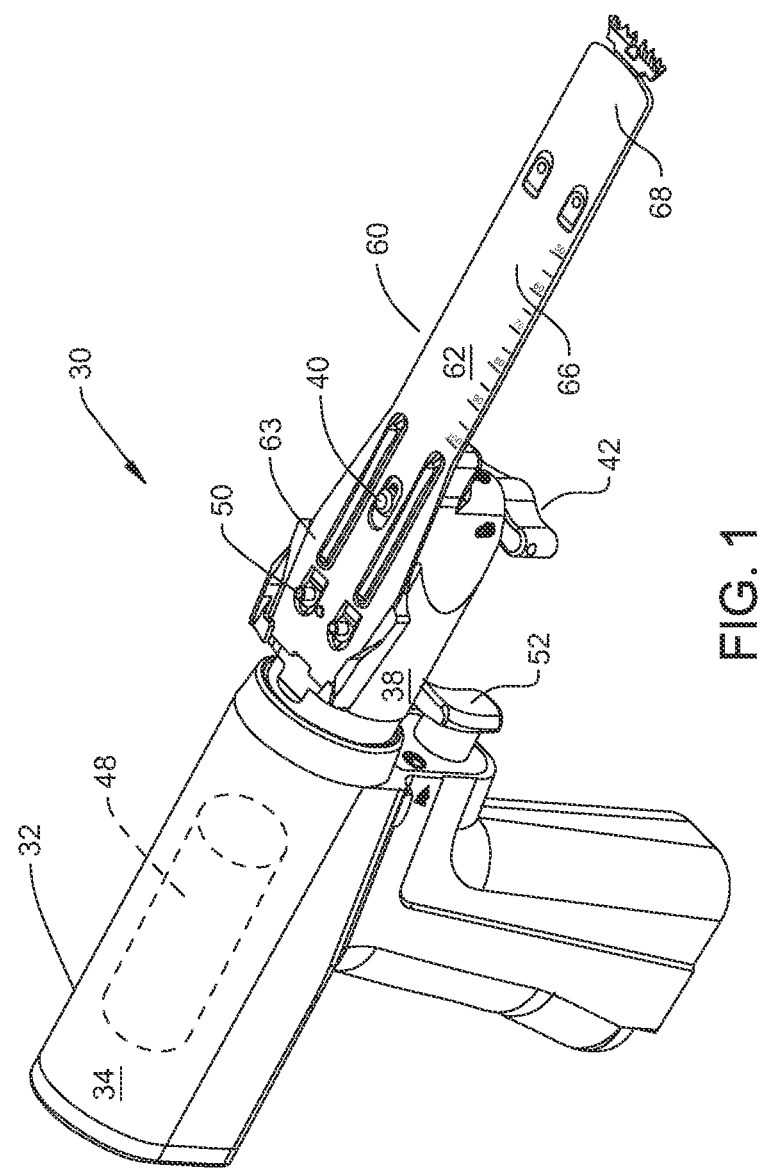
FIG. 1 is a perspective view of a saw and surgical sagittal blade cartridge assembly of this invention.

FIG. 1 depicts an assembly 30 of this invention. Assembly 30 includes a saw 32 to which a surgical sagittal blade cartridge 60 is releasably attached. Saw 32 includes a body or housing 34. In the depicted version of the invention, housing 34 is pistol shaped. The head 38 is shaped to receive the proximal end of cartridge 60. (Here, "proximal" is understood to mean towards the surgeon holding the saw 32; away from the site to which the cartridge 60 is applied. "Distal" is understood to means away from the surgeon holding the saw; towards the site to which the cartridge 60 is applied). A coupling rod 40, the head of which is seen, is slidably mounted to the saw head 38. When coupling rod 40 is in the run position, a portion of the rod presses against the cartridge to hold the cartridge to the head. When the coupling rod 40 is in the load position, the coupling rod 40 does not press against cartridge 60. This allows the cartridge 60 to be removed from the head and a new cartridge releasably attached to the head. A wing nut 42 attached to the head moves the coupling rod 40 between the run and load positions.

A motor 48, represented by a phantom cylinder, is disposed inside the barrel of housing 34. Motor 48 is connected to a pair of drive pins 50, one identified, that are mounted to the head 38 to project above the surface on which the cartridge 60 is seated. The drive pins 50 are mounted to the head 38 to engage in opposed oscillatory motion. A trigger 52, located below the saw head 38, is the manually actuated member that is depressed to control the actuation of the saw. Not seen is the power supply that provides energization signals to the motor 48. Often this power supply is a battery or power cord that is attached to the base of grip portion of the saw housing 34.

Figure 2:
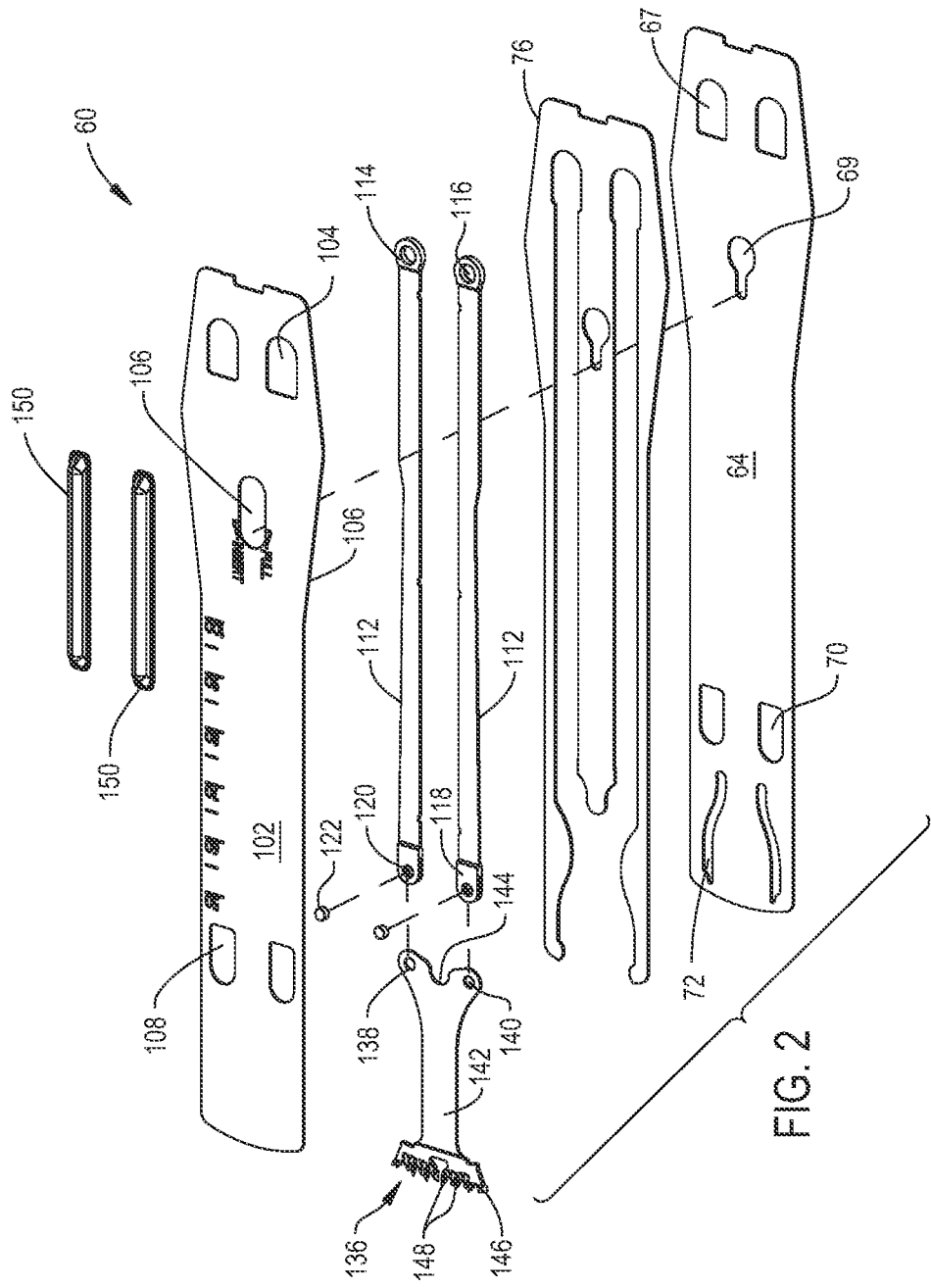
FIG. 2 is an exploded view of the cartridge of this invention.

The cartridge 60, as seen in FIG. 2, includes a guide bar 62 to which a blade 136 is attached. The blade 136 is mounted to and extends forward from the distal section of the guide bar 62. Drive links 112 extend proximally from opposed sides of the blade 136. The drive links 112 terminate at a location forward of the proximal end of the guide bar 62.

The guide bar 62 is a laminate structure that includes a bottom plate 64, an inner plate 76 disposed over the bottom plate 64 and a top plate 102 disposed over the inner plate 76. Inner plate 76 is thus sandwiched between the two outer plates, bottom plate 64 and top plate 102. Collectively, the plates are formed so that the guide bar 62 has a proximal section 63 that from the proximal end of the plate initially tapers outwardly and then tapers inwardly. Forward of the proximal section 63 the guide bar has a middle section 66 and a distal section 68. Plates 64, 76 and 102 are formed so that the opposed sides of the guide bar that form the sides of the middle section and distal sections 68 are parallel. The width across the bar middle and distal sections 66 and 68, respectively, is less that the width across the outwardly tapered portions of the bar proximal section 63.

Immediately forward of the proximal end of the plate, the bottom plate 64 is formed to have two laterally spaced apart openings 67 (one identified). Openings 67 in semi-oval in shape. Each opening 67 has a curved perimeter directed towards the proximal end of the plate and a straight perimeter directed towards the distal end of the cartridge. Forward of openings 67, the bottom plate is formed to have a keyhole shaped opening 69. Opening 69 is shaped so the widest width portion of the opening can receive a head portion of the saw coupling rod 40. Opening 69 is centered along the proximal-to-distal longitudinal axis along the guide bar 62. The bottom plate 64 is further formed so the narrow width portion of the opening 69 is located distally forward of the wide width portion of the opening.

The bottom plate 64 is further formed so that proximal to the distal plate there are two openings 70, one opening identified. Each opening 70 is longitudinally aligned with a separate one of the openings 67. Openings 70 are similar in shape to openings 67 and reverse in orientation relative to openings 67. Openings 70 are thus orientated so the curved ends of the openings 70 face distally. The straight ends of the openings 70 face the proximal end of plate 64. Forward of openings 70, the bottom plate 64 is formed with two elongated slots 72, one slot identified, that extend through the plate. Each slot 72 extends forward from a proximal end located close to the end of the adjacent opening 70 closest to the longitudinal axis along the plate 64. Forward from the proximal end, the slot 72 curves outwardly towards the side edge of the plate. Slots 72 terminate at locations spaced proximally away from the distal end of the plate 64.

Figure 3:
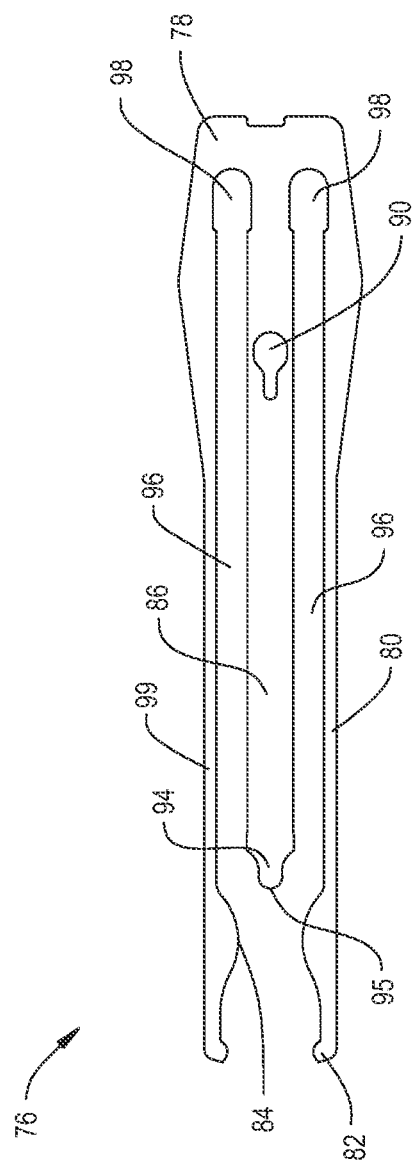
FIG. 3 is a plan view of the inner plate of the cartridge of this invention.

Inner plate 76, as seen best in FIG. 3, is formed to have a base 78 that forms the proximal end of the plate. Three laterally spaced apart tines 80, 86 and 99 extend forward from the base 78. Tines 80 and 99 are the outer tines. The outer surfaces of tines 80 and 99 are the outer surfaces of the plate 76 that form sections of the outer side surfaces of the guide bar 62. Outer tines 80 and 99 thus have proximal sections that extending forward from plate base 78 taper first inwardly and then outwardly. The outer tines 80 and 99 are symmetrically located relative to the longitudinal axis through the guide bar 62. Outer tines 80 and 99 are further shaped to be mirror images each other. Adjacent the distal end of each tine 80 and 99, each tine is shaped to have a tab 82, one identified, that extends inwardly to the longitudinal center axis of the plate 76. Proximal to the tab 82, each tine 80 and 99 is shaped to have a lobe 84, one lobe identified, that extends inwardly towards the longitudinal center axis of the plate 76. Moving proximally to distally along the tine 80 or 99, the associated lobe 84 first curves inwardly and then curves outwardly. The inner plate 76 is formed so that lobes 84 are spaced proximally away from tabs 82.

Tine 86, the inner tine of inner plate 76, is centered on the longitudinal axis of the plate. Tine 86 is formed to have a keyhole shaped opening 90. The inner plate 76 is shaped so that opening 90 is identical in shape and positioned to be in registration with opening 69 of bottom plate 64. The inner tine 86 is of constant width except for the distal end of the tine. At the most distal end, tine 86 has a head 95 with a distally directed face that is curved. Between the constant width section of the tine and the head 95 the tine has a neck 94. The neck 94 has opposed side surfaces that curve inwardly to head 95.

Given that the tines 80, 86 and 99 are spaced apart from each other, there is elongated, closed end slot 96 between each of the outer tines 80 and 99 and the inner tine 88. The proximal end of the slot 96 is the closed end of the slot. When cartridge 60 is assembled, each slot 96 is disposed over a separate one of the openings 67 and 70 in the bottom plate 64. The inner plate 76 is further formed so that the proximal end portion 98 of each slot 96 has a shape substantially equal to the shape of bottom plate openings 67. Thus, the lateral width of the proximal end portion 98 of each slot 96 is greater than the width of the slot 96 distally forward of the proximal section.

Returning to FIG. 2, it is observed that top plate 102 is shaped to have an outer perimeter substantially identical to that of bottom plate 80. Forward of the proximal end of the top plate 102, the plate 102 is shaped to have two openings 104, one opening identified. Openings 104 are identical in shape and positioned to be in registration with bottom plate openings 67. Forward of openings 104, the top plate is formed to have an oval shaped opening 106. Top plate 102 is formed so that when the guide bar 60 is assembled opening 106 is disposed over and extends around inner plate opening 90. The top plate 102 is further formed to define two openings 108, one opening identified. Openings 108 are formed to be identical in shape and in registration over the bottom plate openings 70.

Blade 136 is formed to have a centrally located web 142. The blade 136 is formed so that web 142 has a thickness that is no greater than the thickness of inner plate 76. The web 142 of the blade 136 seen in FIG. 2 is generally rectangular in shape. When blade 136 is in the centered position within the guide bar 62 the major axis of the web 142 is collinear with the major axis of the guide bar. Extending proximally from web 142 and away from the longitudinal axis of the web. Blade 136 is shaped to have two feet 138, one foot identified. Feet 138 have the same thickness of web 142. Each foot 138 extends to the open end of the adjacent slot 96 internal to the inner tine 86. An opening 140 extends top to bottom through each foot 138. Between the feet 138 blade 136 is formed to have a curved, proximally directed face 144. The blade 136 is shaped so that blade face 144 can seat against and pivot around the head 95 integral with the inner tine 86. The blade feet 138 and web 142 are sometimes referred to as the base of the blade 136.

The distal end of the blade web 142 extends to the distal end of the guide bar 60. A head 146 is integrally with and extends forward of the distal end of the web 142. Head 146 is formed with teeth 148. The blade 136 is further formed so that head 142 has a thickness greater than that of the web 142. More particularly, the head is formed to have a thickness so that the kerf formed by the cutting action of blade 136 is sufficient to receive the guide bar 60.

A drive link 112 is disposed in each of the slots 96 internal to the guide bar 62. Each drive link 112 is in the form of an elongated flat strip of metal. The drive links 112 are formed so that, at the proximal end of each link, there is a foot 114, one foot identified. Each foot 114 is formed to have a center located through hole 116, one opening identified. Through holes 116 are dimensioned so that the associated drive rod feet 114 can be fitted over the saw head drive pins 50. Each drive link 112 is shaped so that foot 114 has a thickness that is greater than the thickness of the metal strip forming the main body of the link. The thickness of the feet 114 is typically no greater than the thickness of the guide bar 62. When the cartridge 60 is assembled, the feet 114 generally seat in the proximal end portion 98 of the associated slot 96. The portions of the feet 114 that project outwardly from the main body of each link 112 seat in bottom plate openings 67 and top plate openings 104.

Two fingers 118 extend distally forward from the distal end of the main body of each drive link 112, one finger identified. Fingers 118 overlap and are spaced apart from each other. More particularly, fingers 118 are spaced apart from each a sufficient distance so that a blade foot 138 can seat between each pair of fingers. Each finger 118 is formed with a hole 120. The holes 120 of each pair of fingers 118 are in registration with each other.

As part of the process of assembly a cartridge 60 of this invention, the blade 136 is positioned so that each blade foot 138 is disposed between a pair of drive link fingers 118. A pivot pin 122, one pin identified, that extends through the finger holes 120 and the blade foot opening 140 pivotally holds the foot 38 to the associated drive link 112.

During the assembly of the cartridge 60, the inner plate 76 is initially welded or otherwise secured to the bottom plate 64 or to the top plate 102. After this operation is completed, the drive links-and-blade assembly is positioned so that the drive links 112 are seated in slots 96 and the curved proximally directed face 144 of blade 136 is seated against the curved distally directed face of tine head 95 integral with the inner plate 76. The top plate 102 or bottom plate 64 is then welded or otherwise secured to the exposed face of the inner plate 76. At the completion of the process of assembling the cartridge 60, the drive link feet 114 seat in plate openings 67 and 104. The drive link fingers 118 seat in openings 70 and 108 formed, respectively in the guide bar bottom plate 64 and top plate 102. Blade head 142 is located immediately forward of the distal end of the guide bar 62.

From FIGS. 1 and 2 it can be seen that cartridge 60 includes two parallel ribs 150. Ribs 150 extend upwardly from the outer surface of the bar top plate 102. The ribs are positioned so each rib is aligned with the longitudinal axis of a separate one of the openings 104. Ribs 150 extend forward from a location approximately 2 mm forward of the openings 104. Each rib 150 terminates at a location approximately 10 mm forward of plate opening 106. Ribs 150 are formed separate from the top plate 102. The rib 150 are welded or otherwise permanently secured to the rest of cartridge 60.

As discussed in PCT Pub. No. WO 2013/016472A1/US Pat. Pub. No. 2014/0163558, explicitly incorporated herein by reference, once assembly 30 is prepared for use, cartridge ribs 150 are disposed over saw head 38. Ribs 150 reduce the flexing of the section of cartridge 60 disposed over the saw head 38.

To prepare assembly 30 of this invention for use, the cartridge 60 is fitted to the saw head 38. As a result of this over this attachment, each drive pin 50 is seated in a separate one of the holes 116 formed in a drive link foot 114. Coupling rod 40 extends through the overlapping openings 69, 90 and 106 of the cartridge. The coupling rod 40 is lowered over the guide bar so the head of the coupling rod (not identified) presses against the surface of inner plate 72 exposed through top plate opening 106. This press action holds the cartridge 60 to the saw head 38. When the cartridge 60 is secured to the drive head, the drive pins and drive links cooperate to urge the blade 136 proximally. The proximally directed face 144 of the blade is urged against the curved face of head 95 internal to the cartridge 60.

Assembly 30 is actuated by depressing trigger 52. This results in the actuation of the motor 44. The actuation of the motor 44 results in the back and forth oscillation of the drive pins 50. The movement of the drive pins 50 causes the drive links 112 to engage in opposed back and forth reciprocation of the drive links. The opposed back and forth motion of the drive links 112 causes the blade to pivot back and forth around the head 95 internal to the guide bar 62. The pivoting action of the blade teeth 148 causes the teeth to cut the tissue against which the cartridge is pressed.

During the course of advancing the cartridge 60, the cartridge is exposed to resistive forces. The inner plate 76 provides structural strength to the guide bar 62. This structural strength resists the extent to which the bar 62 would otherwise flex when exposed to these resistive forces. Further reinforcement of the guide bar 62 is provided by the sections of the outer tines 80 and 99 that extend forward of the head 95 of the inner tine 86. Tabs 82 and lobes 84 provide structural strength to the guide bar at the distal portion of the guide bar. This is the portion of the guide bar initially exposed to the resistive forces. The presence of tabs 82 and 84 thus further reduces the likelihood that the distal portion of the guide bar will skive or dive. The prevention of the skiving or diving of this portion of the guide bar 62 reduces the likelihood that the cartridge 60 as whole will skive or dive.

A further feature of this invention is that the drive links 112 are, on both sides, encased in the inner plate 76. This means that, if a surgeon holds or touches the sides of the guide bar when the cartridge is actuated, the surgeon's fingers do not come into contact with the reciprocating driving links 112. At a minimum, this makes it essentially impossible for the drive links to, when moving, tear the glove off the surgeon's fingers. Still another benefit of this construction of the invention, is that it facilitates the efficient welding of the side portions of plates 64, 76 and 102. This side welding of the plates 64, 76 and 102 so as to form side welds along the opposed sides of the guide bar 62 serves to strengthen the guide bar.

Figure 4:
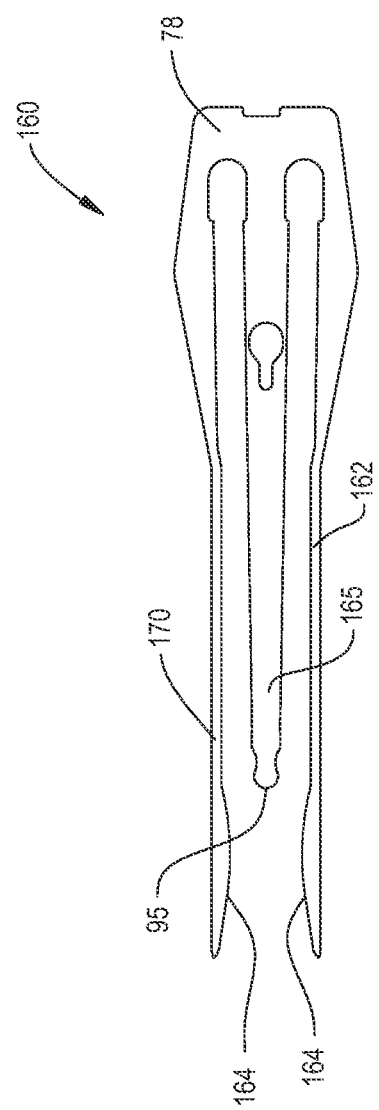
FIG. 4 is a plan view of an alternative inner plate of a cartridge of this invention.

FIG. 4 is a plan view of an alternative inner plate 160 that can be part of guide bar of a cartridge of this invention. Inner plate 160 has the base 78 of the first described inner plate 76. Outer tines 162 and 170 extend forward from the base 78 and are spaced laterally away from the inner tine 86. The proximal portions of outer tines 162 and 170 are identical in shape to the proximal portions of tines 80 and 99. The distal portion of each tine 162 and 170 is only formed with a single member that protrudes inwardly towards the longitudinal axis of the plate 160. This single protrusion is a lobe 164.

Extending proximal to distally along the tine 162 or 170 the lobe extends outwardly from the tine (towards the plate longitudinal axis) from a position slightly proximal to the distal end of the head 95 integral with the inner tine 88. The lobe 164 curves such that where the lobe has a maximum thickness is location forward of head 95. From the position of the maximum thickness, the lobe curves inwardly towards the outer surface of the tine 162 or 170. The distal end of each lobe 164 is the distal end of the tine 162 or 170 with which the lobe is integral.

Inner plate 160 is formed with an inner tine 165. Inner tine 165 is similar in shape to the previously described inner tine 86. A difference between the two tines is that proximal to the neck 95, inner tine 165 has a taper. Thus extending proximally from neck 95 the width of the tine 165 increases.

Inner plate 160 is well suited as the inner plate of a guide bar that is part of cartridge that includes a blade that has a relatively wide web. With this type of cartridge, it may be difficult to provide the tabs 82 of cartridge 60 since the presence of the tabs might interfere with the back and forth oscillations of the web. With a cartridge including lobes 164 the lobes provide the guide bar with the structural strength adjacent in the distal portion of the guide bar that is useful for reducing skiving and diving.

Figure 5:
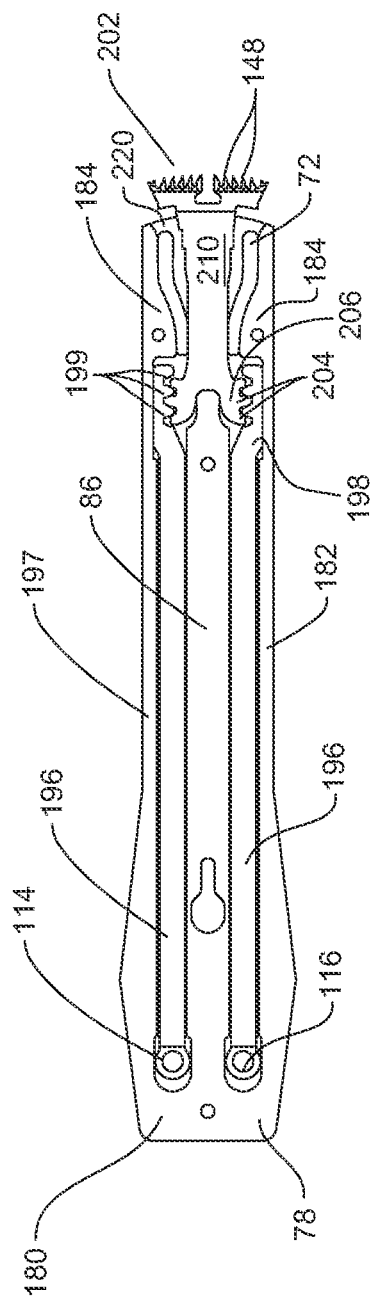
FIG. 5 is a plan view of an alternative assembly that may be integral with the cartridge of this invention.

FIG. 5 illustrates alternative components of a cartridge of this invention. Illustrated here is an inner plate 180. Inner plate 180 has the base 78 and inner tine 86 of the first described inner plate 76. Inner plate 180 has opposed outer tines 182 and 197 that are mirror images from each other. Each tine 182 is formed to have a single lobe 184. Inner plate 180 is formed so that each lobe 184 extends inwardly from the associated tine 182 or 197 at a location distally forward of the tine head 95. Each lobe 184 essentially extends perpendicularly away from the tine 182 or 197. Forward of where the tine 184 extends perpendicularly to the longitudinal axis of the inner plate 180 the lobe starts to taper outwardly away from the longitudinal axis. The distal end of each lobe 184 essentially is the distal end of the tine 182 or 197 with which the lobe is integral. The side to side thickness of the lobes proximal to the distal end of plate 180 is greater than the side to side thickness of the tines 182 and 197 proximal to the lobes.

The inner plate is shown as having a number of through holes, one in the base, one in the inner tine 86 and one in each of the lobes 184, (holes not identified). These holes are present for manufacturing reasons.

A drive link 196 is disposed in each slot between the inner tine 88 and the laterally spaced outer tines 182 and 197. Each drive link has the main body and foot 114 of the first described drive link 112. At the distal end each drive link 196 has a head 198, one head identified. Each head 198 is formed have teeth 199, one set of teeth identified. The drive link teeth 199 are spaced apart from each other along proximal to distal longitudinal axis of the cartridge with which the links 96 are integral A blade 202 is disposed between tine lobes 184. Blade 202 has a web 210. Two legs 206, one leg identified, that are integral with the web 206 extend proximally from the web. Legs 206 are spaced apart from each other so tine head 95 can seat between the legs. The blade 202 is formed so that teeth 204 extend outwardly from legs 206, two teeth identified. Teeth 204 are dimensioned to engage the teeth 199 integral with the adjacent drive link 196. Blade 202 is further formed to have a curved proximally directed face 208 that is located between legs 206 at the distal end of web 210. Face 208 is similar to face 144 of blade 136.

Blade web 210 extends to the distal end of the guide bar. A head 212 is integral with and located forward of the distal end of web 210. Head 210 is functionally the same as blade head 146. Teeth 148 extend forward of head 210

Also seen in FIG. 5 is a portion of the underlying bottom plate 220. Bottom plate 220 is similar in structure to previously described bottom plate 64. Specifically seen are the slots 72 formed in the bottom plate.

When a cartridge having the components of FIG. 5 is assembled, the components are arranged so that blade teeth 204 engage the teeth 198 integral with the driver links 196. The cartridge is used in the same manner in which the previously described cartridge 60 is used. When this cartridge is used, the reciprocal motion of the drive links 196 is transferred to the blade by the engagement of teeth 198. As a result of this engagement the longitudinal back and forth reciprocation of the drive links causes the blade 202 to pivot back and forth around the tine head 95.

It should be understood that the components of the cartridge of FIG. 5 are constructed so that outer tines 182 and 197 restrain the outward lateral movement of the adjacent heads 198 of the drive links 196. More specifically the outer side surfaces of the drive link heads 198 press against the side surfaces of the adjacent drive links 196. This restraining of the motion of the drive link head 198 ensures that, as the links reciprocate to pivot the blade 202, the pivoting movement of the blade legs 206 push the rive link heads 198 away from the adjacent teeth 204. If this action was allowed to occur, it could result in the drive link teeth 199 disengaging from the blade teeth 204.

The above is directed to specific versions of the invention. Alternative versions of the invention may have features different from what has been described.

For example, the various features of the different versions of the invention can be combined.

Likewise not all versions of the invention may have all the described features. There may not be a requirement that is all versions of the invention the outer tines extend forward of the inner tine. In versions of the invention where the outer tines have distal sections that are located forward of the inner tine, it may not be necessary to provide the outer tines with inwardly extends lobes.

Not all versions of the invention may include ribs 150. In some versions of the invention the ribs may be stamped or molded or otherwise integrally formed with the top plate.

Likewise, in some versions of the invention, the inner plate 76 may be wholly or partially formed with one or both of the bottom plate 64 or top plate 102. Thus, in these versions of the invention, once a blank is formed, the blank is machined to define the slots in which the drive rods are seated and that define the perimeter of the tines. Alternatively, the opening- and slot-defining portion of the guide bar may be formed by molding.

In some versions of the invention, a single drive link may be all that is needed to pivot the blade head. In some versions of the invention the one or more drive links may not be parallel to the longitudinal axis through the cartridge. Thus in these versions of the invention, the openings in the guide bar through in which elements of the one or more drive links are seated likewise may not be aligned on line that are parallel to the longitudinal axis through the cartridge.

In versions of the invention in which the at least one drive link and the blade are provided with complementary teeth, the guide bar may have a structure different from what has been described. Specifically the guide bar may be formed so that head are which the blade head is not an integral part of one of the plates forming the bar. In these versions of the invention, the structure around which the blade pivots may be a pin mounted to or integral with at least one of the plates that form the bar.

In some versions of the invention two or all three of the plates that form the guide bar may not be three distinct plates that are welded or otherwise secured together. In these alternative versions of the invention, the plural plates are machined or molded together as a single unit.

The various shapes of the elements may also vary from what has been described.

Accordingly, it is an object of the appended claims to cover all such variations and modifications that cover the true spirit and scope of the invention.

What is claimed is:

1. A surgical saw cartridge for oscillating a blade, the surgical saw cartridge comprising:
   a guide bar including a proximal end and a distal end, the guide bar comprising:
   two outer plates; and
   an inner plate located between the two outer plates, the inner plate defining a base at the proximal end of the guide bar;
   an outer tine disposed between the two outer plates, the outer tine extending distally from the base;
   an inner tine extending distally from the base, the inner tine being disposed between the two outer plates and formed to define a head;
   a blade coupled to the guide bar, the blade formed with teeth located distal to the guide bar and the blade configured to contact and pivot about the head of the inner tine; and
   at least one drive link moveably disposed between the two outer plates within a space between the inner tine and the outer tine, the at least one drive link having opposed proximal and distal ends, the proximal end of the at least one drive link adapted to be attached to a drive element of a saw and the distal end of the at least one drive link being connected to the blade so that reciprocation of the at least one drive link results in pivoting of the blade around the head of the inner tine.

2. The surgical saw cartridge of claim 1, wherein the outer tine comprises a pair of outer tines spaced apart from one another, the pair of outer tines being mirror images of one another.

3. The surgical saw cartridge of claim 2, wherein at least a portion of the blade is located between the pair of outer tines.

4. The surgical saw cartridge of claim 2, wherein the pair of outer tines are symmetrically located relative to a longitudinal axis through the guide bar.

5. The surgical saw cartridge of claim 1, wherein the two outer plates and the inner plate are three separate plates that are secured together to form the guide bar.

6. The surgical saw cartridge of claim 5, wherein an outer surface of the outer tine forms a section of an outer side surface of the guide bar; and
   wherein the guide bar includes a side weld formed along the section of the outer side surface of the guide bar that couples the outer tine to each of the two outer plates.

7. The surgical saw cartridge of claim 1, wherein an outer surface of the outer tine forms a section of an outer side surface of the guide bar; and
   wherein the guide bar includes a side weld formed along the section of the outer side surface of the guide bar that couples the outer tine to each of the two outer plates.

8. The surgical saw cartridge of claim 1, wherein the inner tine defines an opening in registration with an opening of one of the two outer plates.

9. A surgical saw cartridge for oscillating a blade, the surgical saw cartridge comprising:
- a guide bar including a proximal end and a distal end, the guide bar comprising:
  - two outer plates;
  - an inner plate located between the two outer plates;
  - a base that forms a proximal end of the inner plate;
  - two outer tines extending distally from the base and spaced apart from one another;
  - an inner tine that extends distally from the base, the inner tine being disposed between the two outer tines, the inner tine is formed to define a head;
- a blade coupled to the guide bar, the blade formed with teeth located distal to the guide bar and the blade configured to contact and pivot about the head of the inner tine; and
- at least one drive link moveably disposed between the two outer plates within a space between the inner tine and one of the two outer tines, the at least one drive link having opposed proximal and distal ends, the proximal end of the at least one drive link adapted to be attached to a drive element of a saw and the distal end of the at least one drive link being connected to the blade so that reciprocation of the at least one drive link results in pivoting of the blade around the head of the inner tine.

10. The surgical saw cartridge of claim 9, wherein the two outer plates and the inner plate are three separate plates that are secured together to form the guide bar.

* * * * *